(12) United States Patent
Huynh

(10) Patent No.: US 7,592,462 B2
(45) Date of Patent: Sep. 22, 2009

(54) EXPLOSIVE COMPLEXES

(75) Inventor: My Hang V. Huynh, Los Alamos, NM (US)

(73) Assignee: Los Alamos National Security, LLC, Los Alamos, MN (US)

( * ) Notice: Subject to any disclaimer, the term of this patent is extended or adjusted under 35 U.S.C. 154(b) by 173 days.

(21) Appl. No.: 11/707,610

(22) Filed: Feb. 15, 2007

(65) Prior Publication Data

US 2008/0200688 A1    Aug. 21, 2008

(51) Int. Cl.
*C07D 257/00*    (2006.01)
(52) U.S. Cl. ..................................... 548/251
(58) Field of Classification Search ................ 548/251
See application file for complete search history.

(56) References Cited

U.S. PATENT DOCUMENTS

2006/0030715 A1    2/2006    Hiskey et al.

OTHER PUBLICATIONS

T. S. Kon'kova et al, "Thermochemistry of Complex of Transitive Metals with 1,5-Diaminotetrazole as Ligand," *International Annual Conference of ICT* 2000, *31st (Energetic Materials)*, 88/1-88/6.

V. P. Sinditskii et al, "The Structure of Coordination Compounds of Metals with 4-Amino-1,2,4-Triazole as Unidentate Ligand," A. E. *Zhurnal Neorganicheskoi Khimii*, 1987, 32(11), 2726-2729.

L. G. Lavrenova et al, "Complexes of Transition Metals with 1,5-Diaminotetrazole," *Russian Journal of Inorganic Chemistry*, 1988, 33(10), 1480-1482.

P. N. Gaponik et al, "Crystal Structure and Physical Properties of the New 2D Polymeric Compound Bis(1,5-diaminotetrazole)dichlorocopper(II)," *Inorganica Chimica Acta* 2005, 358, 2549-2557.

A. V. Smirnov et al, "Synthesis of Cobalt (III) Ammine Complexes as Explosives for Safe Priming Charge," *Russian Journal of Applied Chemistry* 2004, 77(5), 794-796.

Hirlinger et al., Apr. 2005, Lead Azide Replacement Program, NDIA Fuze Conference.

*Primary Examiner*—REi-tsang Shiao
(74) *Attorney, Agent, or Firm*—Holly L. Teeter; Juliet A. Jones

(57) ABSTRACT

Lead-free primary explosives of the formula $[M^{II}(A)_R(B^X)_S](C^Y)_T$, where A is 1,5-diaminotetrazole, and syntheses thereof are described. Substantially stoichiometric equivalents of the reactants lead to high yields of pure compositions thereby avoiding dangerous purification steps.

7 Claims, 2 Drawing Sheets

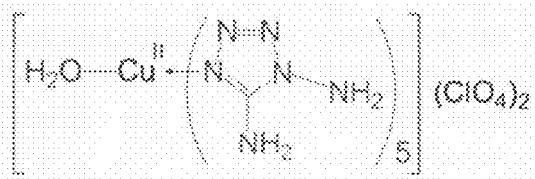
FIGURE 1A
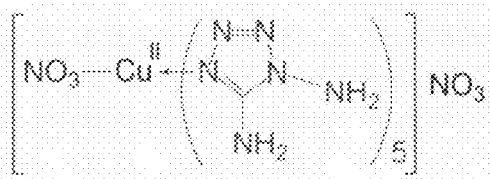
FIGURE 1B
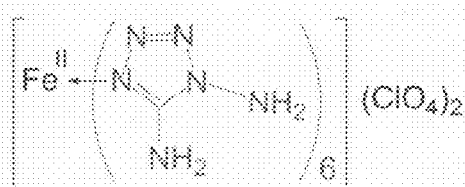
FIGURE 1C
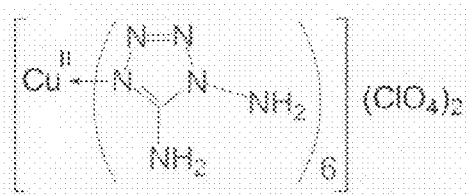
FIGURE 1D
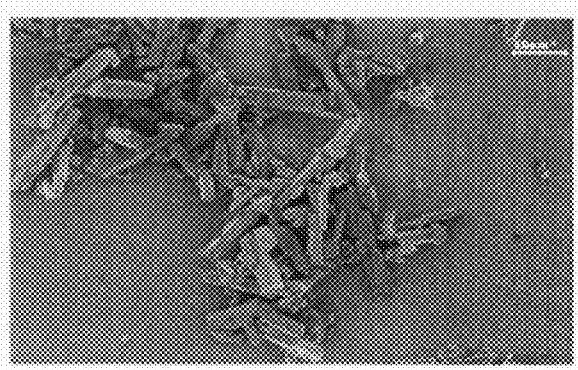
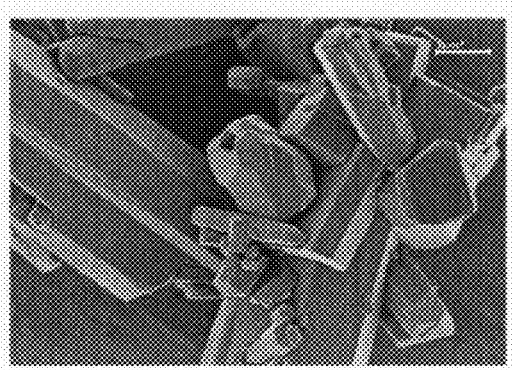
FIGURE 2A: 1 kX (left) and 10 kX (right) of [$Cu^{II}(DAT)_5(H_2O)$]($ClO_4$)$_2$

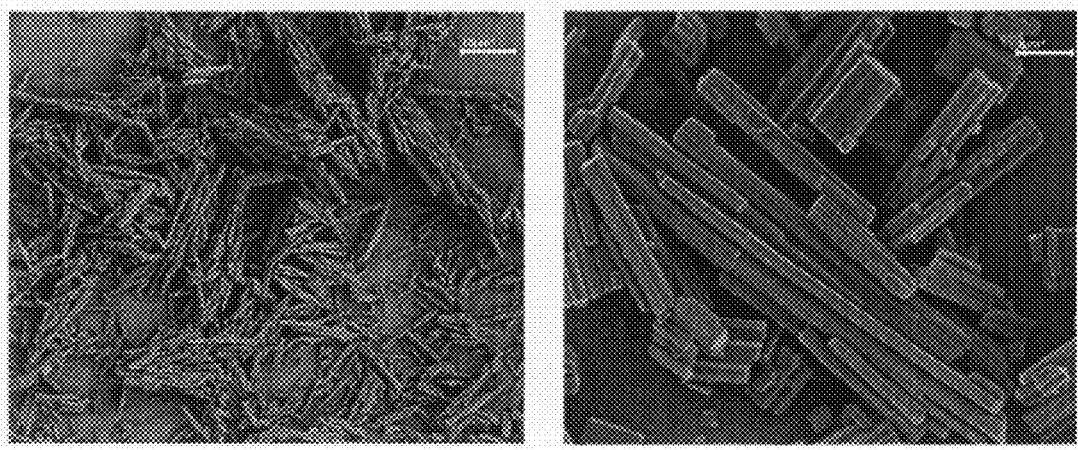
FIGURE 2B: 1 kX (left) and 10 kX (right) of $[Fe^{II}(DAT)_6](ClO_4)_2$
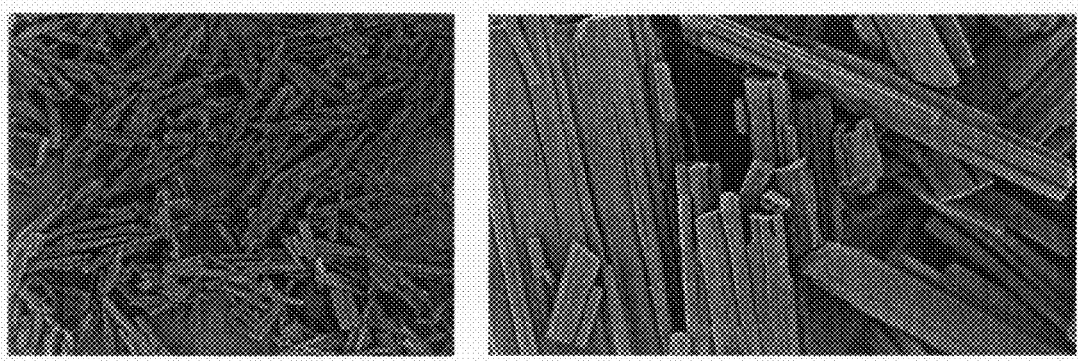
FIGURE 2C: 1 kX (left) and 10 kX (right) of $[Cu^{II}(DAT)_6](ClO_4)_2$

EXPLOSIVE COMPLEXES

STATEMENT OF FEDERAL RIGHTS

The United States government has rights in this invention pursuant to Contract No. DE-AC51-06NA25396 between the United States Department of Energy and Los Alamos National Security, LLC for the operation of Los Alamos National Laboratory.

FIELD OF INVENTION

The present invention relates to lead-free primary explosives.

BACKGROUND

Explosives are categorized as primary or secondary based on their susceptibility to initiation. Primary explosives are highly susceptible to initiation and are used in small quantities to ignite secondary explosives, main charges, propellants, or fuel. Requirements for primary explosives include sufficient sensitivity to be detonated reliably while not being exceedingly dangerous to handle as well as sufficient thermal stability to not decompose on extended storage or thermal insult.

Two common primary explosives are lead azide and lead styphnate, but both emit toxic lead upon detonation. Because of this toxic residue, the development of a lead-free primary explosive is needed.

SUMMARY OF INVENTION

The present invention discloses novel lead-free compounds and syntheses thereof. More particularly, the present invention is directed to compounds of the formula $[M^{II}(A)_R(B^X)_S](C^Y)_T$ and syntheses thereof, wherein M is selected from the group consisting of
(1) cobalt,
(2) copper,
(3) iron,
(4) manganese,
(5) nickel, and
(6) zinc;
A is 1,5-diaminotetrazole ("DAT");
B is selected from the group consisting of
(1) water ("$H_2O$")
(2) 5-aminotetrazole ("AT"),
(3) 5-aminotetrazolate ("$AT^-$"),
(4) 5-nitrotetrazolate ("$NT^-$"),
(5) 3,5-dinitro-1,2,4-triazolate ("$DNT^-$"),
(6) 5-azido-3-nitro-1,2,4-triazolate ("$ANT^-$"),
(7) azide ("$N_3^-$"), and
(8) nitrate ("$NO_3^-$");
C is selected from the group consisting of
(1) $AT^-$,
(2) $ANT^-$,
(3) $DNT^-$,
(4) $NO_3^-$,
(5) $N_3^-$,
(6) $NT^-$,
(7) perchlorate ("$ClO_4^-$"),
(8) tetraazidoborate ("$TAB^-$"),
(9) dinitramide ("$DN^-$"),
(10) nitroformate ("$NF^-$"),
(11) 5,5'-diazido-2,2'-azo-1,3,4-triazolate ("$DAAT^{2-}$"),
(12) 5,5'-dinitro-2,2'-azo-1,3,4-triazolate ("$DNAT^{2-}$"),
(13) 4,4',5,5'-tetranitro-2,2'-biimidazolate ("$TNBI^{2-}$"), and
(14) 5,5'-azotetrazolate ("$AZT^{2-}$");
R is 5 or 6;
S is 0 or 1;
T is 1 or 2;
X is 0 or −1;
Y is −1 or −2;
X+Y=−2; and
R+S=6.

The above compound can be prepared according to the reaction $[M^{II}(H_2O)_6]D_2+R(A)+S(B^X)+T(C^Y) \rightarrow [M^{II}(A)_R(B^X)_S](C^Y)_T$ wherein M is selected from the group consisting of
(1) cobalt,
(2) copper,
(3) iron,
(4) manganese,
(5) nickel, and
(6) zinc;
A is DAT;
B is selected from the group consisting of
(1) $H_2O$,
(2) AT,
(3) $AT^-$,
(4) $NT^-$,
(5) $DNT^-$,
(6) $ANT^-$,
(7) $N_3^-$, and
(8) $NO_3^-$;
C is selected from the group consisting of
(1) $AT^-$,
(2) $ANT^-$,
(3) $DNT^-$,
(4) $NO_3^-$,
(5) $N_3^-$,
(6) $NT^-$,
(7) $ClO_4^-$,
(8) $TAB^-$,
(9) $DN^-$,
(10) $NF^-$,
(11) $DAAT^{2-}$,
(12) $DNAT^{2-}$,
(13) $TNBI^{2-}$, and
(14) $AZT^{2-}$;
D is selected from the group consisting of
(1) $ClO_4^-$,
(2) $NO_3^-$, and
(3) $Cl^-$;
R is 5 or 6;
S is 0 or 1;
T is 1 or 2;
X is 0 or −1;
Y is −1 or −2;
X+Y=−2; and
R+S=6 as follows:
(1) mixing a chosen quantity of a metal salt $[M^{II}(H_2O)_6]D_2$ and R molar equivalents of A in a suitable solvent, thereby forming a first solution;
(2) heating said first solution at a time and temperature suitable for the color of said first solution to change;
(3) adding S molar equivalents of $B^X$ to said first solution, thereby forming a second solution;

(4) heating said second solution at a time and temperature suitable for generating a third solution containing a cationic complex;
(5) adding T molar equivalents of $C^Y$ to said third solution containing said cationic complex at a time and temperature suitable to form said compound;
(6) cooling said third solution to room temperature; and
(7) separating said compound from said third solution.

BRIEF DESCRIPTION OF THE DRAWINGS

FIG. 1A shows a copper embodiment of the lead-free compound $[Cu^{II}(DAT)_5(H_2O)](ClO_4)_2$.

FIG. 1B shows a copper embodiment of the lead-free compound $[Cu^{II}(DAT)_5(NO_3)]NO_3$.

FIG. 1C shows an iron embodiment of the lead-free compound $[Fe^{II}(DAT)_6](ClO_4)_2$.

FIG. 1D shows a copper embodiment of the lead-free compound $[Cu^{II}(DAT)_6](ClO_4)_2$.

FIG. 2A shows two scanning electron microscope outputs for the copper embodiment of the lead-free compound $[Cu^{II}(DAT)_5(H_2O)](ClO_4)_2$. The left output has a magnification of 1,000. The right output has a magnification of 10,000.

FIG. 2B shows two scanning electron microscope outputs for the iron embodiment of the lead-free compound $[Fe^{II}(DAT)_6](ClO_4)_2$. The left output has a magnification of 1,000. The right output has a magnification of 10,000.

FIG. 2C shows two scanning electron microscope outputs for the copper embodiment of the lead-free compound $[Cu^{II}(DAT)_6](ClO_4)_2$. The left output has a magnification of 1,000. The right output has a magnification of 10,000.

DETAILED DESCRIPTION

The present invention is directed to compounds of the formula $[M^{II}(A)_R(B^X)_S](C^Y)_T$ and syntheses thereof, wherein
M is selected from the group consisting of
(1) cobalt,
(2) copper,
(3) iron,
(4) manganese,
(5) nickel, and
(6) zinc;
A is DAT;
B is selected from the group consisting of
(1) $H_2O$,
(2) AT,
(3) $AT^-$,
(4) $NT^-$,
(5) $DNT^-$,
(6) $ANT^-$,
(7) $N_3^-$, and
(8) $NO_3^-$;
C is selected from the group consisting of
(1) $AT^-$,
(2) $ANT^-$,
(3) $DNT^-$,
(4) $NO_3^-$,
(5) $N_3^-$,
(6) $NT^-$,
(7) $ClO_4^-$,
(8) $TAB^-$,
(9) $DN^-$,
(10) $NF^-$,
(11) $DAAT^{2-}$,
(12) $DNAT^{2-}$,
(13) $TNBI^{2-}$, and
(14) $AZT^{2-}$;
R is 5 or 6;
S is 0 or 1;
T is 1 or 2;
X is 0 or −1;
Y is −1 or −2;
X+Y=−2; and
R+S=6.

The above compound can be prepared according to the reaction $[M^{II}(H_2O)_6]D_2 + R(A) + S(B^X) + T(C^Y) \rightarrow [M^{II}(A)_R(B^X)_S](C^Y)_T$ wherein
M is selected from the group consisting of
(1) cobalt,
(2) copper,
(3) iron,
(4) manganese,
(5) nickel, and
(6) zinc;
A is DAT;
B is selected from the group consisting of
(1) $H_2O$,
(2) AT,
(3) $AT^-$,
(4) $NT^-$,
(5) $DNT^-$,
(6) $ANT^-$,
(7) $N_3^-$, and
(8) $NO_3^-$;
C is selected from the group consisting of
(1) $AT^-$,
(2) $ANT^-$,
(3) $DNT^-$,
(4) $NO_3^-$,
(5) $N_3^-$,
(6) $NT^-$,
(7) $ClO_4^-$,
(8) $TAB^-$,
(9) $DN^-$,
(10) $NF^-$,
(11) $DAAT^{2-}$,
(12) $DNAT^{2-}$,
(13) $TNBI^{2-}$, and
(14) $AZT^{2-}$;
D is selected from the group consisting of
(1) $ClO_4^-$,
(2) $NO_3^-$, and
(3) $Cl^-$;
R is 5 or 6;
S is 0 or 1;
T is 1 or 2;
X is 0 or −1;
Y is −1 or −2;
X+Y=−2; and
R+S=6 as follows:
(1) mixing a chosen quantity of a metal salt $[M^{II}(H_2O)_6]D_2$ and R molar equivalents of A in a suitable solvent, thereby forming a first solution;
(2) heating said first solution at a time and temperature suitable for the color of said first solution to change;
(3) adding S molar equivalents of $B^X$ to said first solution, thereby forming a second solution;
(4) heating said second solution at a time and temperature suitable for generating a third solution containing a cationic complex;

(5) adding T molar equivalents of $C^Y$ to said third solution containing said cationic complex at a time and temperature suitable to form said compound;

(6) cooling said third solution to room temperature; and (7) separating said compound from said third solution.

In step 1, a suitable solvent is an ethanolic solvent or an acidic ethanolic solvent (a mixture of absolute ethanol and two drops of acid with a pH measurement ranging from about 0 to about 2). In step 4, the second solution can be heated anywhere from about above room temperature to reflux and for a time in the range of from about 30 minutes to 3 hours or until the solution becomes colorless. In step 6, the third solution is preferably slowly cooled to 40° C. with gentle stirring, and then the third solution is allowed to cool to room temperature undisturbed. Gentle stirring can achieve small particle sizes for subsequent safe handling. Depending on the nature of $C^Y$, the ethanolic reaction solution may be reduced in volume, or the temperature is lowered using an ice-bath to precipitate the compound.

Dangerous purification steps can be avoided by employing an absolute ethanolic solvent and stoichiometric equivalents of the reactants to form a nearly quantitative single product. An acidic solvent or excess quantity of any reactant might result in impurities.

Reference is now made in detail to four embodiments of the invention. These four embodiments are $[Cu^{II}(DAT)_5(H_2O)](ClO_4)_2$, $[Cu^{II}(DAT)_5(NO_3)]NO_3$, $[Fe^{II}(DAT)_6](ClO_4)_2$, and $[Cu^{II}(DAT)_6](ClO_4)_2$ which may have the configurations shown in FIGS. 1A-1D.

The embodiment of $[Cu^{II}(DAT)_5(H_2O)](ClO_4)_2$ can be prepared by refluxing a solution of copper salt having the formula $[Cu^{II}(H_2O)_6](ClO_4)_2$ and 5 molar equivalents of DAT in a suitable solvent. The resulting precipitate is filtered and washed thoroughly with fresh, cold ethanol. The reaction gives nearly quantitative yield and an analytically pure product of $[Cu^{II}(DAT)_5(H_2O)](ClO_4)_2$ without additional recrystallization or purification.

The embodiment of $[Cu^{II}(DAT)_5(NO_3)]NO_3$ can be prepared by refluxing a solution of a copper salt having the formula $[Cu^{II}(H_2O)_6](NO_3)_2$ and 5 molar equivalents of DAT in a suitable solvent. The resulting precipitate is filtered and washed thoroughly with fresh, cold ethanol. The reaction gives nearly quantitative yield and an analytically pure product of $[Cu^{II}(DAT)_5(NO_3)](-NO_3-)$ without additional recrystallization or purification.

The embodiment of $[Fe^{II}(DAT)_6](ClO_4)_2$ can be prepared by refluxing a solution of an iron salt having the formula $[Fe^{II}(H_2O)_6](ClO_4)_2$ and 6 molar equivalents of DAT in a suitable solvent. The resulting precipitate is filtered and washed thoroughly with fresh, cold ethanol. The reaction gives nearly quantitative yield and an analytically pure product of $[Fe^{II}(DAT)_6](ClO_4)_2$ without additional recrystallization or purification.

The embodiment of $[Cu^{II}(DAT)_6](ClO_4)_2$ can be prepared by refluxing a solution of a copper salt having the formula $[Cu^{II}(H_2O)_6](ClO_4)_2$ and 6 molar equivalents of DAT in a suitable solvent. The resulting precipitate is filtered and washed thoroughly with fresh, cold ethanol. The reaction gives nearly quantitative yield and an analytically pure product of $[Cu^{II}(DAT)_6](ClO_4)_2$ without additional recrystallization or purification.

EXAMPLE 1

Preparation of —$[Cu^{II}(DAT)_5(H_2O)](ClO_4)_2$

A copper compound was prepared in accordance with the reaction $[Cu^{II}(H_2O)_6](ClO_4)_2 + 5\ DAT \rightarrow [Cu^{II}(DAT)_5(H_2O)](ClO_4)_2$ as follows:

(a) 0.15 grams ("g") of cupric perchlorate was completely dissolved in 40 milliliters ("mL") of absolute ethanol;

(b) 0.203 g of DAT was slowly added to the solution of cupric perchlorate;

(c) the resulting solution was heated to reflux for between 2 hours and 3 hours or until the mother liquor was completely clear and colorless;

(d) the solution was cooled to about 40° C. with slow stirring and then allowed to cool to room temperature undisturbed;

(e) the precipitate was filtered out of the mother liquor, thereby accumulating a collected solid;

(f) the collected solid was washed thoroughly with fresh, cold, absolute ethanol;

(g) the undried collected solid was wet transferred into a Teflon-vial using a plastic spatula with care taken to avoid scraping or friction between the spatula and walls of the vial; and (h) the collected solid was air-dried prior to use.

Elemental analysis of the collected solid, as set forth in TABLE 1, showed the composition corresponds to $[Cu^{II}(DAT)_5(H_2O)](ClO_4)_2$.

TABLE 1

|  | CARBON (%) | HYDROGEN (%) | NITROGEN (%) |
| --- | --- | --- | --- |
| THEORETICAL | 7.69 | 2.84 | 53.81 |
| OBSERVED | 7.54 ± 0.4 | 2.57 ± 0.4 | 51.18 ± 0.4 |

The above-described synthesis yielded about 91% $[Cu^{II}(DAT)_5(H_2O)](ClO_4)_2$.

FIG. 2A shows two scanning electron microscope outputs for the copper embodiment of the lead-free compound $[Cu^{II}(DAT)_5(H_2O)](ClO_4)_2$. The left output has a magnification of 1,000. The right output has a magnification of 10,000.

The density of the copper compound was 1.98 grams per cubic centimeter ("g/cm$^3$") using a liquid pycnometry technique. The thermal decomposition temperature was 224° C. (on a 5-7 microgram ("μg") sample) as determined by Differential Scanning Calorimetry ("DSC").

Explosive initiation data of the dry collected solid were as follows:

Friction: 15 g determined on a 1-1.5 milligram ("mg") sample using mini BAM;

Impact: 5 cm on a 5 mg sample determined by a type 12 impact machine;

Spark: 0.06875 joules ("J") determined by ABL Electrostatic Discharge.

EXAMPLE 2

Preparation of $[Cu^{II}(DAT)_5(NO_3)]NO_3$

A copper compound was prepared in accordance with the reaction $[Cu^{II}(H_2O)_6](NO_3)_2 + 5\ DAT \rightarrow [Cu^{II}(DAT)_5(NO_3)]NO_3$ as follows:

(a) 0.30 g of cupric nitrate was completely dissolved in 40 mL of absolute ethanol;

(b) 0.405 g of DAT was slowly added to the solution of cupric nitrate;

(c) the resulting solution was heated to reflux for between 2 hours and 3 hours or until the mother liquor was completely clear and colorless;

(d) the solution was cooled to about 40° C. with slow stirring and then allowed to cool to room temperature undisturbed;

(e) the precipitate was filtered out of the mother liquor, thereby accumulating a collected solid;

(f) the collected solid was washed thoroughly with fresh, cold, absolute ethanol;

(g) the undried collected solid was wet transferred into a Teflon-vial using a plastic spatula with care taken to avoid scraping or friction between the spatula and walls of the vial; and (h) the collected solid was air-dried prior to use.

Elemental analysis of the collected solid, as set forth in TABLE 2, showed the composition corresponds to $[Cu^{II}(DAT)_5(NO_3)]NO_3$.

TABLE 2

| | CARBON (%) | HYDROGEN (%) | NITROGEN (%) |
|---|---|---|---|
| THEORETICAL | 8.73 | 2.93 | 65.15 |
| OBSERVED | 8.77 ± 0.4 | 2.82 ± 0.4 | 63.23 ± 0.4 |

The above-described synthesis yielded about 94% $[Cu^{II}(DAT)_5(NO_3)]NO_3$.

The density of the copper compound was 2.08 g/cm³ using a liquid pycnometry technique. The thermal decomposition temperature was 228° C. (on a 7-8 µg sample) as determined by DSC.

Explosive initiation data of the dry collected solid were as follows:

Friction: 2.0 kg determined on a 1-1.5 mg sample using BAM;

Impact: 10 cm on a 5 mg sample determined by a type 12 impact machine;

Spark: 3.125 J determined by ABL Electrostatic Discharge.

EXAMPLE 3

Preparation of $[Fe^{II}(DAT)_6](ClO_4)_2$

An iron compound was prepared in accordance with the reaction $[Fe^{II}(H_2O)_6](ClO_4)_2 + 6\ DAT \rightarrow [Fe^{II}(DAT)_6](ClO_4)_2$ as follows:

(a) 0.20 g of ferrous perchlorate was completely dissolved in 40 mL of absolute ethanol;

(b) 0.331 g of DAT was slowly added to the solution of ferrous perchlorate;

(c) the resulting solution was heated to reflux for between 2 hours and 3 hours or until the mother liquor was completely clear and colorless;

(d) the solution was cooled to about 40° C. with slow stirring and then allowed to cool to room temperature undisturbed;

(e) the precipitate was filtered out of the mother liquor, thereby accumulating a collected solid;

(f) the collected solid was washed thoroughly with fresh, cold, absolute ethanol;

(g) the undried collected solid was wet transferred into a Teflon-vial using a plastic spatula with care taken to avoid scraping or friction between the spatula and walls of the vial; and (h) the collected solid was air-dried prior to use.

Elemental analysis of the collected solid, as set forth in TABLE 3, showed the composition corresponds to $[Fe^{II}(DAT)_6](ClO_4)_2$.

TABLE 3

| | CARBON (%) | HYDROGEN (%) | NITROGEN (%) |
|---|---|---|---|
| THEORETICAL | 8.43 | 2.83 | 58.96 |
| OBSERVED | 8.60 ± 0.4 | 2.92 ± 0.4 | 58.23 ± 0.4 |

The above-described synthesis yielded about 93% $[Fe^{II}(DAT)_6](ClO_4)_2$.

FIG. 2B shows two scanning electron microscope outputs for the iron embodiment of the lead-free compound having a formula $[Fe^{II}(DAT)_6](ClO_4)_2$. The left output has a magnification of 1,000. The right output has a magnification of 10,000.

The density of the iron compound was 2.03 g/cm³ using a liquid pycnometry technique. The thermal decomposition temperature was 194° C. (on a 4-5 µg sample) as determined by DSC.

Explosive initiation data of the dry collected solid were as follows:

Friction: <10 g determined on a 1-1.5 mg sample using mini BAM;

Impact: 5 cm on a 5 mg sample determined by a type 12 impact machine;

Spark: 0.0375 J determined by ABL Electrostatic Discharge.

EXAMPLE 4

Preparation of $[Cu^{II}(DAT)_6](ClO_4)_2$

A copper compound was prepared in accordance with the reaction $[Cu^{II}(H_2O)_6](ClO_4)_2 + 6\ DAT \rightarrow [Cu^{II}(DAT)_6](ClO_4)_2$ in a manner similar to that described in EXAMPLE 1 for the preparation of $[Cu^{II}(DAT)_5(H_2O)](ClO_4)_2$ herein above, except that 6 molar equivalents of DAT are used in step (b).

Elemental analysis of the collected solid, as set forth in TABLE 4, showed the composition corresponds to $[Cu^{II}(DAT)_6](ClO_4)_2$.

TABLE 4

| | CARBON (%) | HYDROGEN (%) | NITROGEN (%) |
|---|---|---|---|
| THEORETICAL | 8.35 | 2.80 | 58.43 |
| OBSERVED | 7.97 ± 0.4 | 2.64 ± 0.4 | 54.43 ± 0.4 |

The above-described synthesis yielded about 94% $[Cu^{II}(DAT)_6](ClO_4)_2$.

FIG. 2C shows two scanning electron microscope outputs for a copper embodiment of the lead-free compound having a formula $[Cu^{II}(DAT)_6](ClO_4)_2$. The left output has a magnification of 1,000. The right output has a magnification of 10,000.

The density of the copper compound was 2.14 g/cm³ using a liquid pycnometry technique. The thermal decomposition temperature was 232° C. (on a 4-5 µg) as determined by DSC.

Explosive initiation data of the dry collected solid were as follows:

Friction: <10 g determined on a 1-1.5 mg sample using mini BAM;

Impact: 5 cm on a 5 mg sample determined by a type 12 impact machine;

Spark: 0.03125 J determined by ABL Electrostatic Discharge.

It is understood that the foregoing detailed description and examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to chemical structures, syntheses, formulations and/or methods of use of the invention, may be made without departing from the spirit and scope thereof.

I claim:

1. A compound of formula $[M^{II}(A)_R(B^X)_S](C^Y)_T$ wherein M is selected from the group consisting of
   (1) cobalt,
   (2) copper,
   (3) iron,
   (4) manganese,
   (5) nickel, and
   (6) zinc;

A is DAT;

B is selected from the group consisting of
   (1) $H_2O$,
   (2) $N_3^-$, and
   (3) $NO_3^-$;

C is selected from the group consisting of
   (1) $NO_3^-$,
   (2) $N_3^-$,
   (3) $NT^-$,
   (4) $ClO_4^-$,
   (5) $DN^-$,
   (6) $NF^-$, and
   (7) $AZT^{2-}$;

R is 5 or 6;
S is 0 or 1;
T is 1 or 2;
X is 0 or −1;
Y is −1 or −2;
X+Y=−2; and
R+S=6.

2. The compound of claim 1 wherein R is 6.
3. The compound of claim 2 wherein M is iron.
4. The compound of claim 3 wherein C is $NT^-$.
5. The compound of claim 1 wherein R is 5.
6. The compound of claim 1 wherein M is iron.
7. The compound of claim 6 wherein R is 6.

\* \* \* \* \*